(12) United States Patent
Shimomura et al.

(10) Patent No.: US 6,920,352 B2
(45) Date of Patent: Jul. 19, 2005

(54) METHOD AND SYSTEM FOR ESTIMATING VISCERAL FAT AREA

(75) Inventors: Miyuki Shimomura, Tokyo (JP); Miyuki Kodama, Tokyo (JP); Hitoshi Sato, Tsurugashima (JP)

(73) Assignee: Tanita Corporation, Tokyo (JP)

(*) Notice: Subject to any disclaimer, the term of this patent is extended or adjusted under 35 U.S.C. 154(b) by 53 days.

(21) Appl. No.: 10/193,281

(22) Filed: Jul. 12, 2002

(65) Prior Publication Data

US 2003/0013982 A1 Jan. 16, 2003

(30) Foreign Application Priority Data

Jul. 12, 2001 (JP) ........................................ 2001-212790

(51) Int. Cl.[7] .............................................. A61B 5/05
(52) U.S. Cl. ...................................................... 600/547
(58) Field of Search ................................ 600/547, 300, 600/587; 128/897; 33/512, 511

(56) References Cited

U.S. PATENT DOCUMENTS

| 4,880,014 A | 11/1989 | Zarowitz et al. |
| 5,579,782 A | 12/1996 | Masuo |
| 5,611,351 A | * 3/1997 | Sato et al. ................... 600/547 |
| 6,468,209 B1 | * 10/2002 | Heymsfield et al. ........ 600/300 |
| 6,487,445 B1 | * 11/2002 | Serita et al. ................. 600/547 |

FOREIGN PATENT DOCUMENTS

| CN | 1277007 | 12/2000 |
| CN | 1293944 | 5/2001 |
| EP | 1 063 500 | 12/2000 |
| EP | 1 063 500 A2 | 12/2000 |
| EP | 1 095 613 | 5/2001 |
| EP | 1 232 724 | 8/2002 |
| EP | 1 249 205 | 10/2002 |

* cited by examiner

Primary Examiner—Max F. Hindenburg
Assistant Examiner—Brian Szmal
(74) Attorney, Agent, or Firm—McDermott Will & Emery LLP

(57) ABSTRACT

A visceral fat area estimating system of the present invention comprises first input unit for inputting a height of an subject, second input unit for inputting a body weight of the subject, third input unit for inputting a fat mass of the subject, fourth input unit for inputting age of the subject, computation unit for computing a visceral fat area based on data from the first, second, third and fourth input unit, and display unit for displaying the visceral fat area computed by the computation unit. Therefore, the system can estimate a visceral fat area securely without concern for exposure of an subject to X-rays, at low costs, and with proper accuracy.

14 Claims, 15 Drawing Sheets

FIG.15

RESULTS OF MEASUREMENTS

| SEX : MALE | AGE : XX YEARS OLD | HEIGHT : YYYcm |
|---|---|---|
| BODY WEIGHT : 56.0kg | AVERAGE BODY WEIGHT : 54.0kg | BMI : 23.7 |

| PERCENT BODY FAT : 20.5% | FAT FREE MASS : 52.0kg | PROPER RANGES | PERCENT FAT : 17.0~23.0% |
|---|---|---|---|
| FAT MASS : 18.0kg | | | FAT MASS : 9.9~14.4kg |

| | RIGHT HAND | RIGHT FOOT | LEFT HAND | LEFT FOOT | TRUNK |
|---|---|---|---|---|---|
| IMPEDANCE | | | | | |
| PARTIAL PERCENT BODY FAT | | | | | |
| PARTIAL FAT MASS | | | | | |

VISCERAL FAT AREA

METHOD AND SYSTEM FOR ESTIMATING VISCERAL FAT AREA

BACKGROUND OF THE INVENTION (i) Field of the Invention

The present invention relates to a method and system for estimating a visceral fat area. More specifically, it relates to a method and system for estimating a visceral fat area by use of a bioelectrical impedance.

(ii) Description of the Related Art

In recent years, accumulation of visceral fat has been receiving attention as a factor which exerts a significant influence on health and causes the onset of a lifestyle-related disease. An example of means for knowing accumulation of visceral fat is a method for estimating a visceral fat area by means of X-ray CT. However, to practice the method, assistance of a radiological technician is essential due to use of X-rays. This keeps the method from being widely used. Further, the method cannot be said to be favorable in that it causes an subject to be exposed to X-rays. In addition, the method also has a problem that its operation costs are excessively high.

Meanwhile, there is a correlation between a abdominal circumference on a navel and a visceral fat area, and there is a method for estimating a visceral fat area by use of the correlation.

However, a measurement value of the abdominal circumference on the navel is significantly influenced by where the circumference is measured, a degree of tension in the abdominal part, timing of the measurement, i.e., before or after meal, and a condition of an subject such as a position of the subject. Therefore, when a visceral fat area is to be estimated based on only the measurement value or with emphasis on the measurement value, the estimation is liable to be influenced by the above measurement conditions. Further, when an subject tries to measure a abdominal circumference on a navel by himself/herself, the subject is liable to tense his/her abdominal part at the time of the measurement or make the measurement off a proper position.

SUMMARY OF THE INVENTION

An object of the present invention is to provide a method and system for estimating a visceral fat area with which anyone can estimate a visceral fat area securely without concern for exposure to X-rays, at low costs, and with proper accuracy.

According to one aspect of the present invention, there is provided a method for estimating a visceral fat area of an subject based on an equation which takes a height, body weight, fat mass and age of the subject as parameters.

According to one embodiment of the present invention, when the height is expressed as H, the body weight as Wt, the fat mass as FM, the age as Age, the visceral fat area as VFA and constants as $C_1$, $C_2$, $C_3$ and $C_4$, the equation is expressed as $$VFA = C_1 \times H^2/Wt + C_2 \times FM + C_3 \times Age + C_4.$$

According to another embodiment of the present invention, when the height is expressed as H, the body weight as Wt, the fat mass as FM, the age as Age, the visceral fat area as VFA and constants as $C_{21}$, $C_{22}$, $C_{23}$ and $C_{24}$, the equation is expressed as $$VFA = C_{21} \times H/Wt + C_{22} \times FM + C_{23} \times Age + C_{24}.$$

According to another embodiment of the present invention, when the height is expressed as H, the body weight as Wt, the fat mass as FM, the age as Age, the visceral fat area as VFA and constants as $C_{31}$, $C_{32}$, $C_{33}$ and $C_{34}$, the equation is expressed as $$VFA = C_{33} \times H^3/Wt + C_{32} \times FM + C_{33} \times Age + C_{34}.$$

According to another embodiment of the present invention, when the height is expressed as H, the body weight as Wt, the fat mass as FM, the age as Age, the visceral fat area as VFA and constants as $C_{41}$, $C_{42}$, $C_{43}$, $C_{44}$ and $C_{45}$, the equation is expressed as $$VFA = C_{41} \times H + C_{42} \times Wt + C_{43} \times FM + C_{44} \times Age + C_{45}.$$

According to another aspect of the present invention, there is provided a method for estimating a visceral fat area of an subject based on an equation which is expressed as $$VFA = C_1 \times H^2/Wt + C_2 \times FM + C_3 \times Age + C_4$$

when a height of the subject is expressed as H, a body weight as Wt, a fat mass as FM, age as AGE, a visceral fat area as VFA and constants as $C_1$, $C_2$, $C_3$ and $C_4$.

According to one embodiment of the present invention, the fat mass is calculated based on a bioelectrical impedance between two body parts of the subject.

According to another embodiment of the present invention, the two body parts are both feet.

According to another embodiment of the present invention, the two body parts are both hands.

According to another embodiment of the present invention, the two body parts are a hand and a foot.

According to another embodiment of the present invention, the fat mass is a fat mass of a trunk.

According to another embodiment of the present invention, in the equation, a correction is made based on at least one of personal parameters which are intensity of daily activity, presence or absence of menstruation, age at the onset of menopause and the number of years elapsed after the onset of menopause.

According to one aspect of the present invention, there is provided a system for estimating a visceral fat area, the system comprising first input unit, second input unit, third input unit, fourth input unit, computation unit and display unit, wherein said first input unit inputs a height of an subject, said second input unit inputs a body weight of the subject, said third input unit inputs a fat mass of the subject, said fourth input unit inputs age of the subject, said computation unit computes a visceral fat area based on data from the first, second, third and fourth input unit, and said display unit displays the visceral fat area computed by the computation unit.

According to one embodiment of the present invention, the first input unit is a height measuring device.

According to another embodiment of the present invention, the first input unit is key input unit for inputting the height manually.

According to another embodiment of the present invention, the second input unit is a weight sensor.

According to another embodiment of the present invention, the second input unit is key input unit for inputting the body weight of the subject manually.

According to another embodiment of the present invention, the third input unit is an body fat meter.

According to another embodiment of the present invention, the third input unit is key input unit for inputting the fat mass of the subject manually.

According to another embodiment of the present invention, the second and third input unit are a scale equipped with an body fat meter.

According to another embodiment of the present invention, the computation unit performs the computation based on an equation expressed as $$VFA = C_1 \times H^2/Wt + C_2 \times FM + C_3 \times Age + C_4$$

when the height of the subject is expressed as H, the body weight as Wt, the fat mass as FM, the age as Age, the visceral fat area as VFA and constants as $C_1$, $C_2$, $C_3$ and $C_4$.

According to another embodiment of the present invention, the computation unit performs the computation based on an equation expressed as $$VFA = C_{21} \times H/Wt + C_{22} \times FM + C_{23} \times Age + C_{24}$$

when the height of the subject is expressed as H, the body weight as Wt, the fat mass as FM, the age as Age, the visceral fat area as VFA and constants as $C_{21}$, $C_{22}$, $C_{23}$ and $C_{24}$.

According to another embodiment of the present invention, the computation unit performs the computation based on an equation expressed as $$VFA = C_{31} \times H^3/Wt + C_{32} \times FM + C_{33} \times Age + C_{34}$$

when the height of the subject is expressed as H, the body weight as Wt, the fat mass as FM, the age as Age, the visceral fat area as VFA and constants as $C_{31}$, $C_{32}$, $C_{33}$ and $C_{34}$.

According to another embodiment of the present invention, the computation unit performs the computation based on an equation expressed as $$VFA = C_{41} \times H + C_{42} \times Wt + C_{43} \times FM + C_{44} \times Age + C_{45}$$

when the height of the subject is expressed as H, the body weight as Wt, the fat mass as FM, the age as Age, the visceral fat area as VFA and constants as $C_{41}$, $C_{42}$, $C_{43}$, $C_{44}$ and $C_{45}$.

According to another aspect of the present invention, there is provided a system for estimating a visceral fat area, the system comprising first key input unit, a weight sensor, an body fat meter, second key input unit, computation unit and display unit wherein said first key input unit inputs a height of an subject manually, said weight sensor measures a body weight of the subject, said body fat meter measures a fat mass of the subject, said second key input unit inputs age of the subject manually, said computation unit computes a visceral fat area based on an equation expressed as $$VFA = C_1 \times H^2/Wt + C_2 \times FM + C_3 \times Age + C_4$$

when the height from the first key input unit is expressed as H, the age from the second key input unit as Age, the body weight from the weight sensor as Wt, the fat mass from the body fat meter as FM, the visceral fat area as VFA and constants as $C_1$, $C_2$, $C_3$ and $C_4$, and said display unit displays the visceral fat area computed by the computation unit.

According to one embodiment of the present invention, the fat mass is calculated based on a bioelectrical impedance between two body parts of the subject.

According to another embodiment of the present invention, the two body parts are both feet.

According to another embodiment of the present invention, the two body parts are both hands.

According to another embodiment of the present invention, the two body parts are a hand and a foot.

According to another embodiment of the present invention, the fat mass is a fat mass of a trunk.

According to another embodiment of the present invention, in the computation of the visceral fat area, the computation unit makes a correction based on at least one of personal parameters which are intensity of daily activity, presence or absence of menstruation, age at the onset of menopause and the number of years elapsed after the onset of menopause.

BRIEF DESCRIPTION OF THE DRAWINGS

FIG. 15 is a diagram showing an example of measurement values and values calculated from the measurement values displayed on the visceral fat area estimating system of FIGS. 12 A and B.

Figure 1:
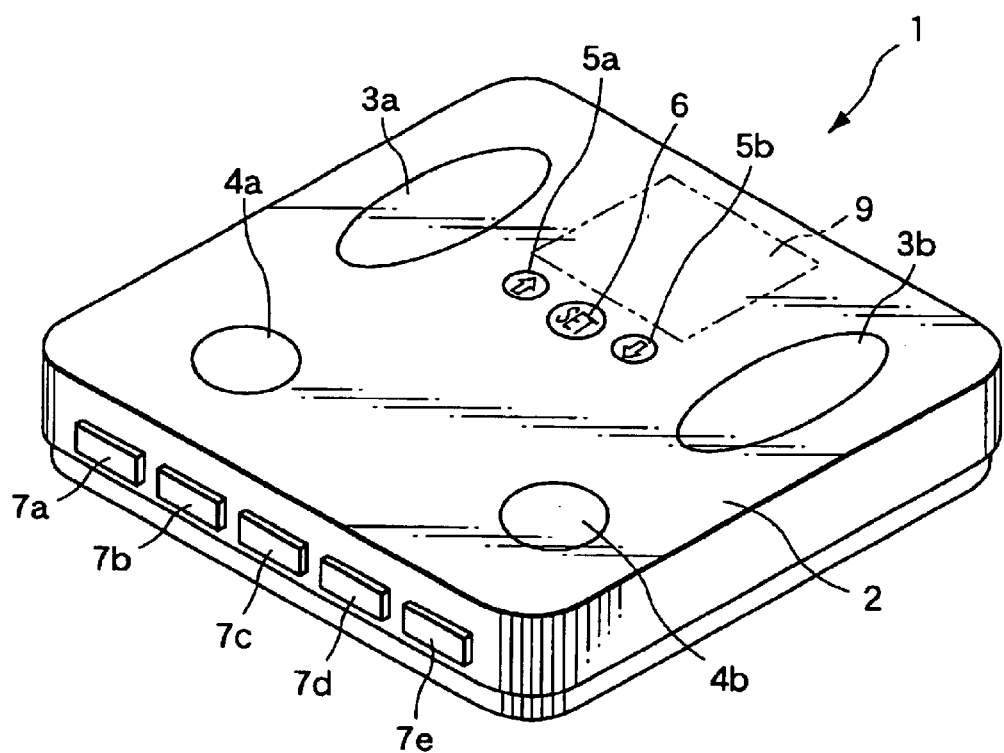
FIG. 1 is a schematic perspective view of an external appearance of a visceral fat area estimating system as one embodiment of the present invention.

Reference numerals 1 and 60 denote a visceral fat area estimating system; 2 a platform; 3a, 3b, 58a and 58b a current-carrying electrode; 4a, 4b, 59a and 59b a measuring electrode; 5a an UP key; 5b a DOWN key; 6 a setting key; 7a to 7e a personal key; 9 a display unit; 10 an electrode switching unit; 15 a weight sensor; 20 an electronic circuit board; 21 a high frequency constant current circuit; 22 a voltage measuring circuit; 23 an A/D converter; 24 a microprocessor; and 25 a memory.

DETAILED DESCRIPTION OF THE PREFERRED EMBODIMENT

Next, embodiments of the present invention will be described in detail with reference to the attached drawings.

Firstly, a method for estimating a visceral fat area which underlies the present invention will be described.

The present inventor has made regression analyses on a visceral fat area determined by X-ray CT, age, a height, a body weight, BMI, and a fat mass determined by a bioelectrical impedance method. BMI is an abbreviation for "Body Mass Index". More specifically, it is a value obtained by dividing a body weight (kg) by a square of a height (m).

Figure 5:
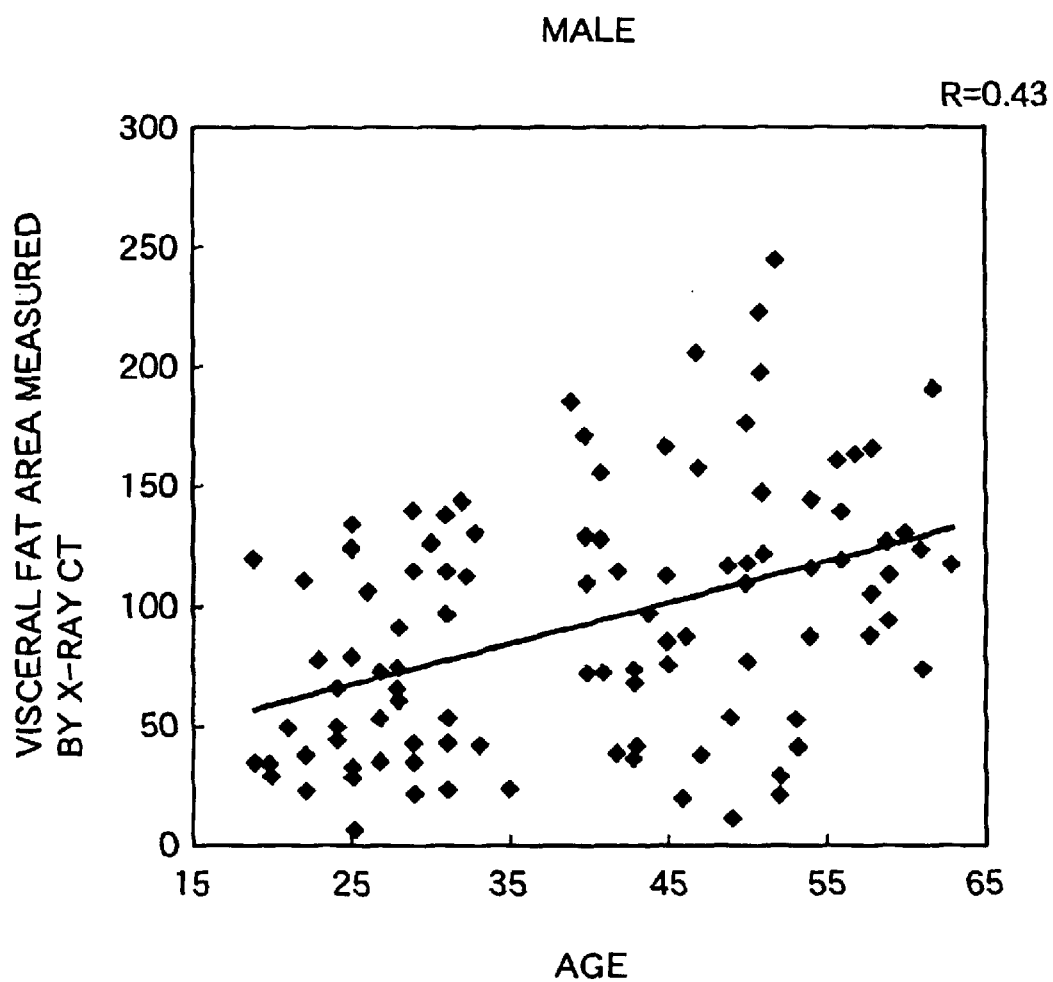
FIG. 5 is a diagram showing ages and visceral fat areas measured by X-ray CT plotted on a graph.
Figure 6:
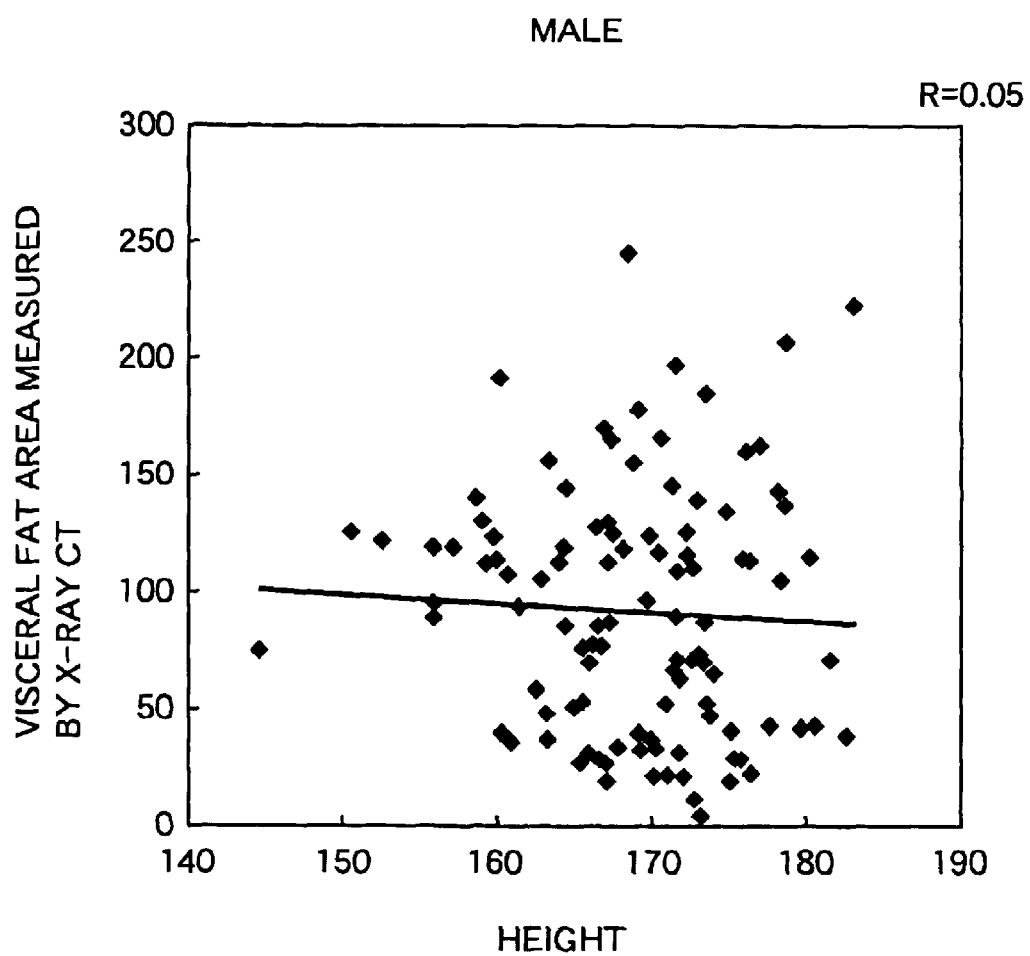
FIG. 6 is a diagram showing heights and visceral fat areas measured by X-ray CT plotted on a graph.
Figure 7:
FIG. 7 is a diagram showing body weights and visceral fat areas measured by X-ray CT plotted on a graph.
Figure 8:
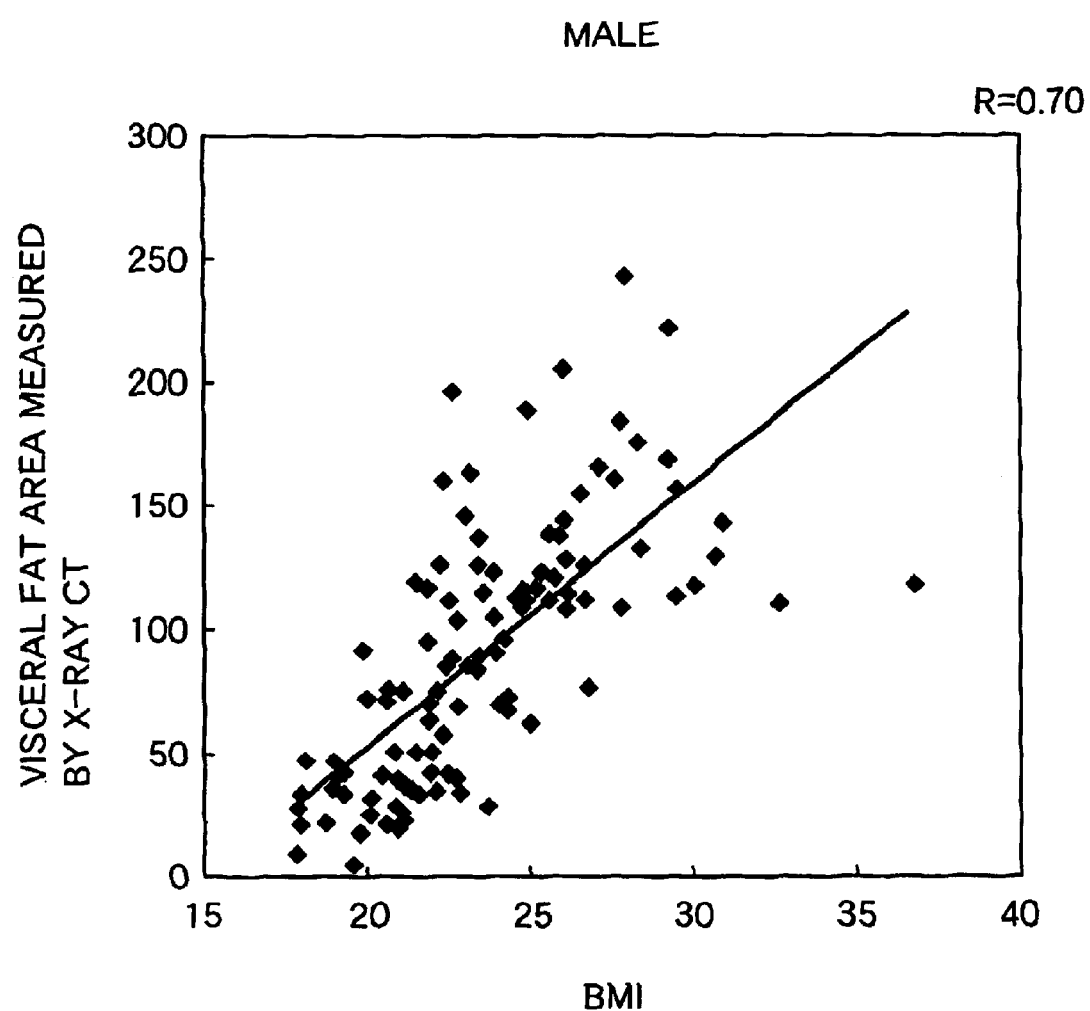
FIG. 8 is a diagram showing BMIs and visceral fat areas measured by X-ray CT plotted on a graph.
Figure 9:
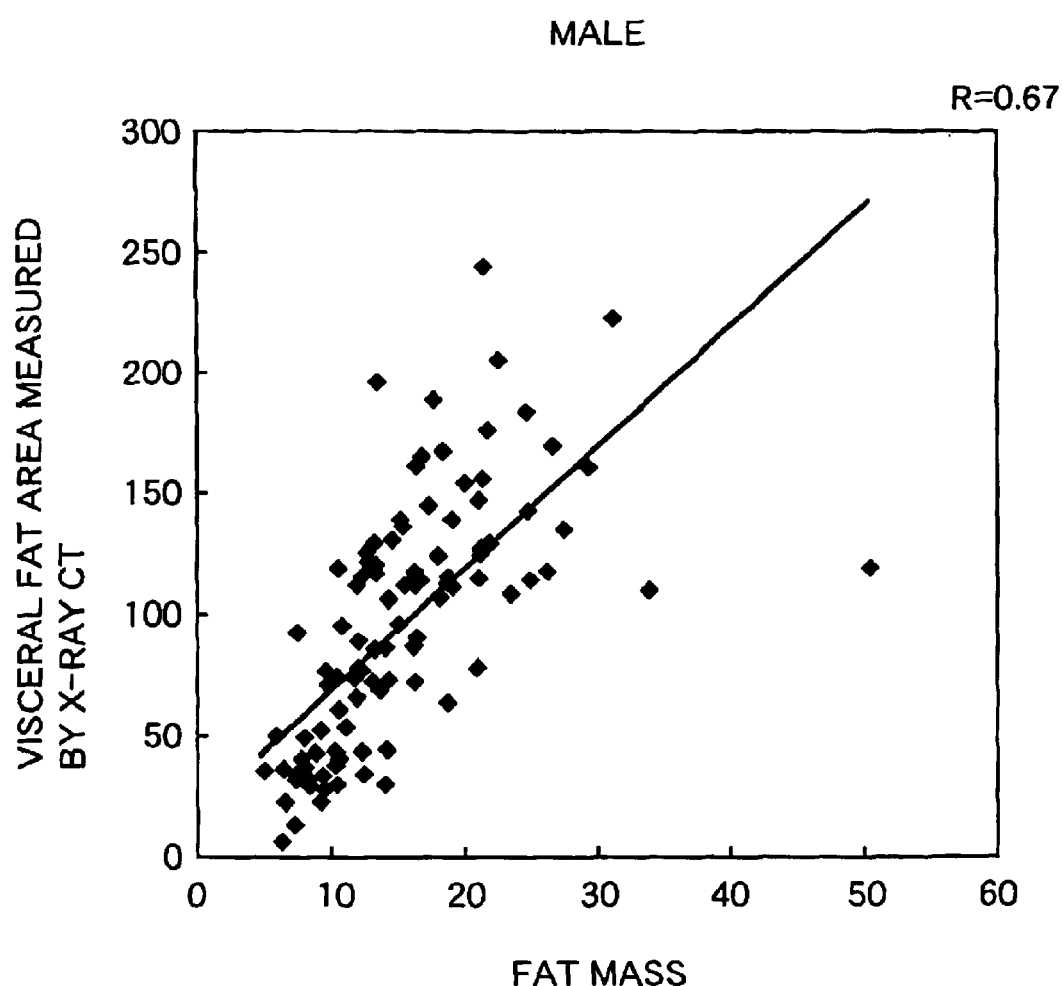
FIG. 9 is a diagram showing visceral fat areas measured by X-ray CT and fat masses measured by a bioelectrical impedance method plotted on a graph.

FIG. 5 is a graph showing a correlation between the visceral fat areas determined by X-ray CT and ages of males. A correlation coefficient is 0.43. Similarly, FIG. 6 is a graph showing a correlation between the visceral fat areas determined by X-ray CT and heights of the males. A correlation coefficient is 0.05. FIG. 7 is a graph showing a correlation between the visceral fat areas determined by X-ray CT and body weights of the males. A correlation coefficient is 0.60. FIG. 8 is a graph showing a correlation between the visceral fat areas determined by X-ray CT and BMIs of the males. A correlation coefficient is 0.70. FIG. 9 is a graph showing a correlation between the visceral fat areas determined by X-ray CT and fat masses of the males. A correlation coefficient is 0.67.

Figure 10:
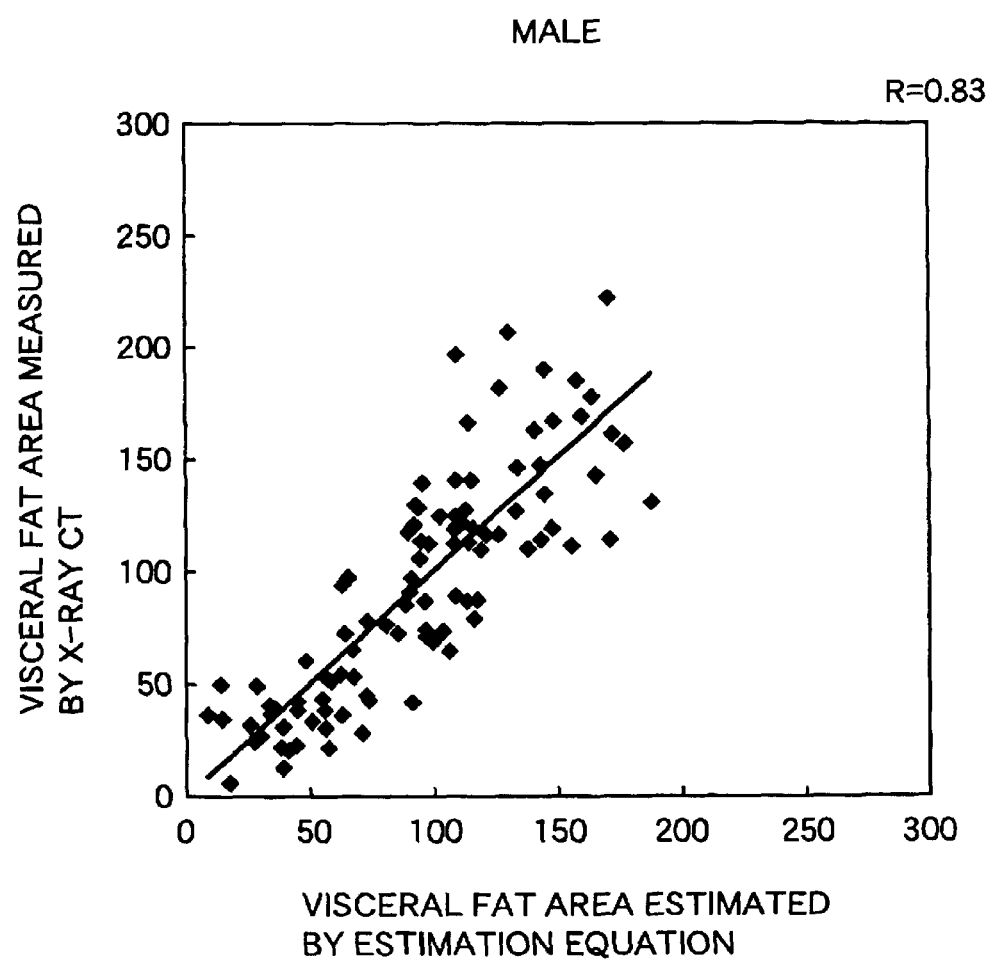
FIG. 10 is a diagram showing visceral fat areas measured by X-ray CT and visceral fat areas estimated by a bioelectrical impedance method for males plotted on a graph.
Figure 11:
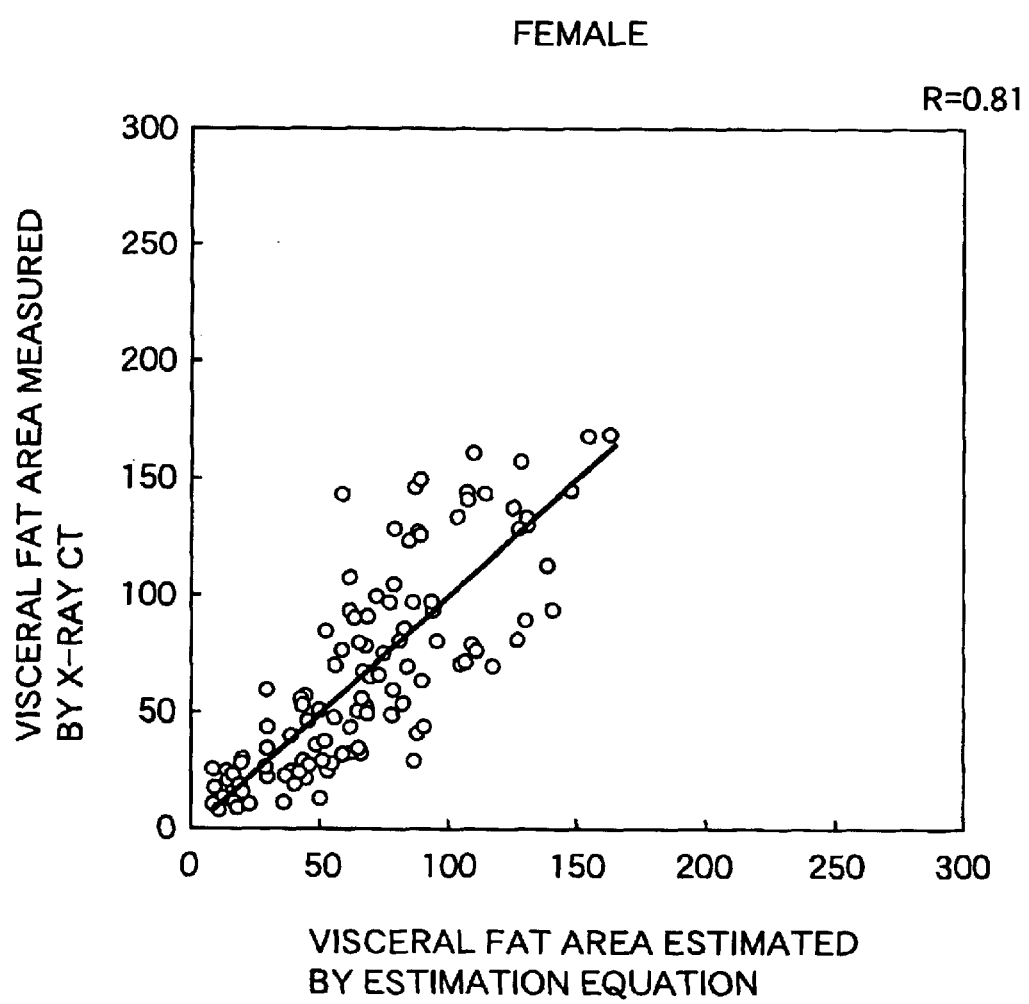
FIG. 11 is a diagram showing visceral fat areas measured by X-ray CT and visceral fat areas estimated by a bioelectrical impedance method for females plotted on a graph.

Then, multiple regression analyses are performed by use of VFA which represents the visceral fat areas as an object variable and, as explanatory variables, H which represents the heights, Wt which represents the body weights, FM which represents the fat masses, and AGE which represents the ages. In the case of the males, a multiple correlation coefficient is 0.83 as shown in FIG. 10. In the case of females, a multiple correlation coefficient is 0.81 as shown in FIG. 11.

From these correlations, the following regression equation can be obtained.

$$VFA = C_1 \times H^2/Wt + C_2 \times FM + C_3 \times Age + C_4 \qquad (1)$$

wherein $C_1$ to $C_4$ are constants. Therefore, a visceral fat area VFA can be obtained by substitution of a height, body weight, age, and FM determined from a bioelectrical impedance into the equation (1).

It is known that the constants $C_1$ to $C_4$ vary according to personal parameters including intensity of daily activity, presence or absence of menstruation, age at the onset of menopause and the number of years elapsed after the onset of menopause. Therefore, when a correction is made based on such personal parameters, a visceral fat area can be estimated more accurately.

Next, a system for estimating a visceral fat area as one of the embodiments of the present invention as described above will be described.

Figure 2:
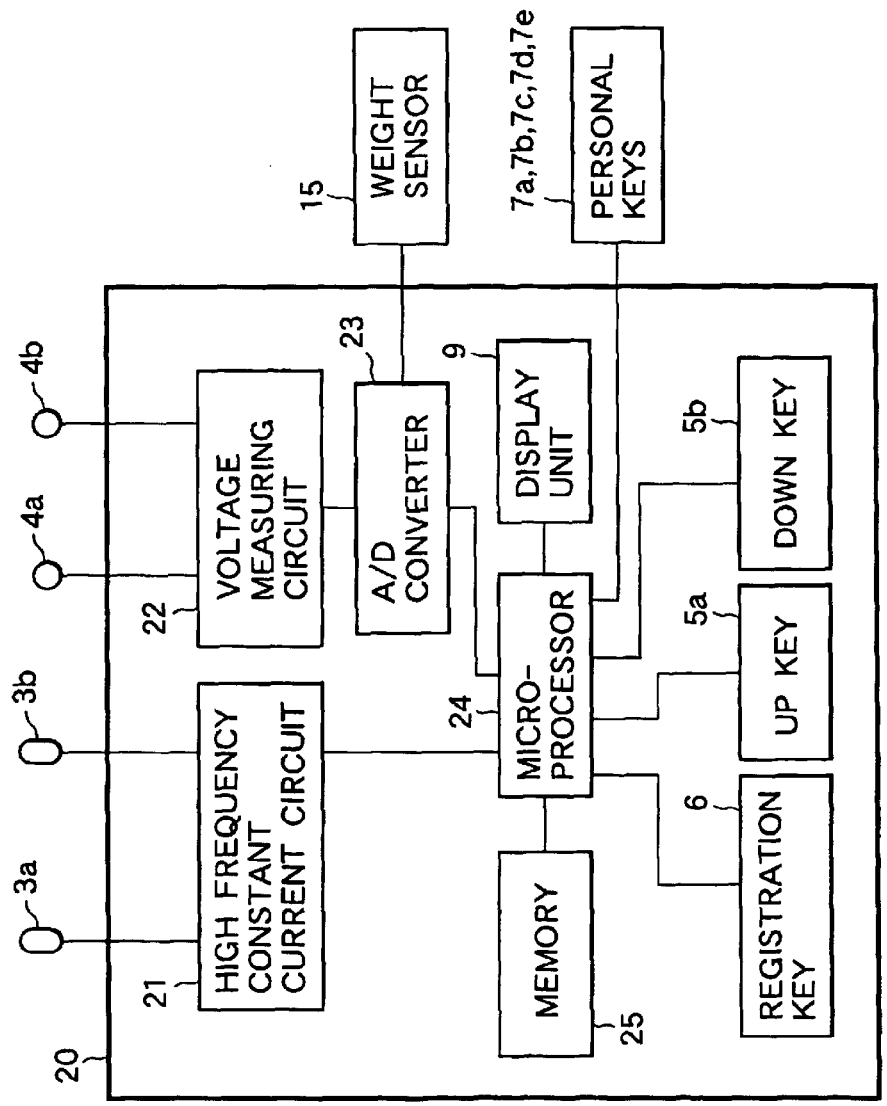
FIG. 2 is a block diagram showing an electric circuit arrangement of the visceral fat area estimating system of FIG. 1.

FIG. 1 is a schematic perspective view of an external appearance of the visceral fat area estimating system. FIG. 2 is a block diagram showing an electric circuit arrangement of the system of FIG. 1. An estimating system 1 of the present embodiment has, on a weighing platform 2 of a scale, current-carrying electrodes 3a and 3b for forming a current path in a living body, measuring electrodes 4a and 4b for detecting a potential difference which occurs in the living body, a setting key 6 for setting personal data including a height, age and gender as well as time, an UP key 5a for incrementing a numerical value, a DOWN key 5b for decrementing a numerical value, personal keys 7a to 7e for making a measurement based on retrieved personal data, and a display unit 9 for displaying statuses of set conditions, results of measurements or results of determinations. Further, as shown in FIG. 2, inside the platform 2, a weight sensor 15 for detecting a load and converting it into an electric signal, an electronic circuit board 20 and the like are provided. The personal keys 7a to 7e and the setting key 6 also serve as a power switch. Upon press of any one of the personal keys 7a to 7e or the setting key 6, the system is activated. Meanwhile, the system is deactivated after passage of a certain period of time after a result of measurement is displayed or even during entry of data.

The electronic circuit board 20 has the display unit 9 provided on the platform 2, the setting key 6, the UP key 5a, the DOWN key 5b, a high frequency low current circuit 21 for applying a very weak constant current of high frequency to the current-carrying electrodes 3a and 3b, a voltage measuring circuit 22 for measuring a potential difference in a living body which occurs between the measuring electrodes 4a and 4b, an A/D conversion circuit 23 for converting an analog signal from the voltage measuring circuit 22 or weight sensor 15 into a digital signal, a memory 25 for storing set and registered conditions, measured data and the like, and a microprocessor 24 for computing a percent body fat and the like based on measurement conditions, measured bioelectrical impedance data and body weight data and controlling. The electronic circuit board 20 is connected to each of the current-carrying electrodes 3a and 3b, measuring electrodes 4a and 4b, weight sensor 15 and personal keys 7a, 7b, 7c and 7d via an electric wire.

Figure 3:
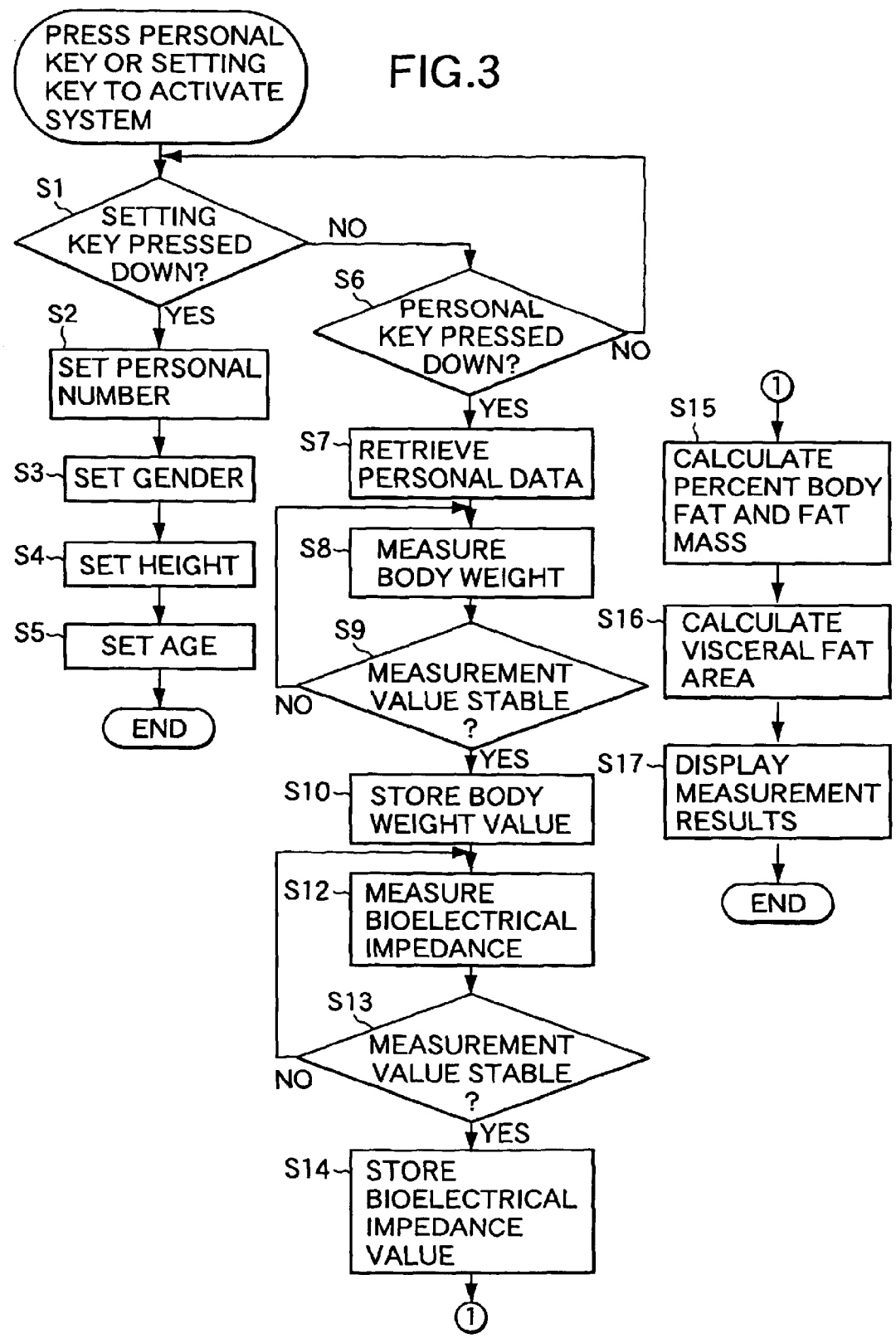
FIG. 3 is a flowchart illustrating steps for making measurements required to estimate a visceral fat area and for estimating the visceral fat area as well as an outline of operations of the visceral fat area estimating system of FIG. 1.

FIG. 3 is a flowchart illustrating steps for estimating a visceral fat area and an outline of operations of the visceral fat area estimating system in the present embodiment. Hereinafter, an overall operation will be described with reference to the flowchart. STEPS S2 to S5 will be described briefly since these are prior arts. Upon press of any one of the personal keys 7a to 7e or the setting key 6, the system is activated. When the setting key 6 is pressed down, settings of personal data including a height, age and gender can be made. Meanwhile, when one of the personal keys is pressed down, personal data set by means of the setting key is read from the memory 25, and a measurement is made based on the data. In STEP S1, it is determined whether the setting key 6 has been pressed down. If a key other than the setting key 6 has been pressed down, the system proceeds to STEP S6. In STEP S2, a personal number to be set is entered. On the display unit 9, a personal number "1" is displayed. Each time the UP key 5a is pressed, the personal number is incremented by 1. Meanwhile, each time the DOWN key 5b is pressed, the personal number is decremented by 1. Upon press of the setting key 6, the personal number is set and then stored in the memory 25. In STEP S3, gender is entered and set in the same manner as the personal number has been set. In STEP S4, a height is set. In this STEP, since an initial value of the height is displayed on the display unit 9, the height value can be incremented and decremented by use of the UP key 5a and the DOWN key 5b, respectively. When the value reaches a desired value, the height value is confirmed by press of the setting key 6. In STEP S5, age is set in the same manner as the height has been set. Then, the program is terminated.

In STEP S6, if none of the personal keys 7a to 7e has been pressed down, the system returns to STEP S1. In STEP S7, personal data such as gender and a height which corresponds to a pressed personal key is read from the memory 25 and displayed on the display unit 9 to encourage an subject to check whether he has pressed down a right personal key. In STEP S8, when the subject stands on the platform 2, his body weight is measured. In STEP S9, if a stable measurement value cannot be obtained, the system returns to STEP S8. In STEP S10, the weight value is stored in the memory 25.

In STEP S12, a bioelectrical impedance is measured in the following manner. That is, the high frequency constant current circuit 21 outputs a very weak constant current I of high frequency. This output current is applied to the subject via the current-carrying electrodes 3a and 3b. At this time, the current passing through the subject is detected by the voltage measuring circuit 22 as a potential difference in the living body which occurs between the measuring electrodes 4a and 4b. This analog output is converted to a digital signal V by the A/D converter 23. A bioelectrical impedance Z is determined by an equation Z=V/I. In STEP S13, if a stable measurement value cannot be obtained, the system returns to STEP S12. In STEP S14, the measured bioelectrical impedance value is stored in the memory 25.

Then, the system proceeds to STEP S15 in which a percent body fat is calculated from the body weight, the height and the bioelectrical impedance value measured in STEP S12. Description of a method for calculating the percent body fat will be omitted since it is known to those skilled in the art. To determine a fat mass, the body weight is multiplied by the percent body fat.

In STEP S16, a visceral fat area is estimated by use of the equation (1).

Figure 4:
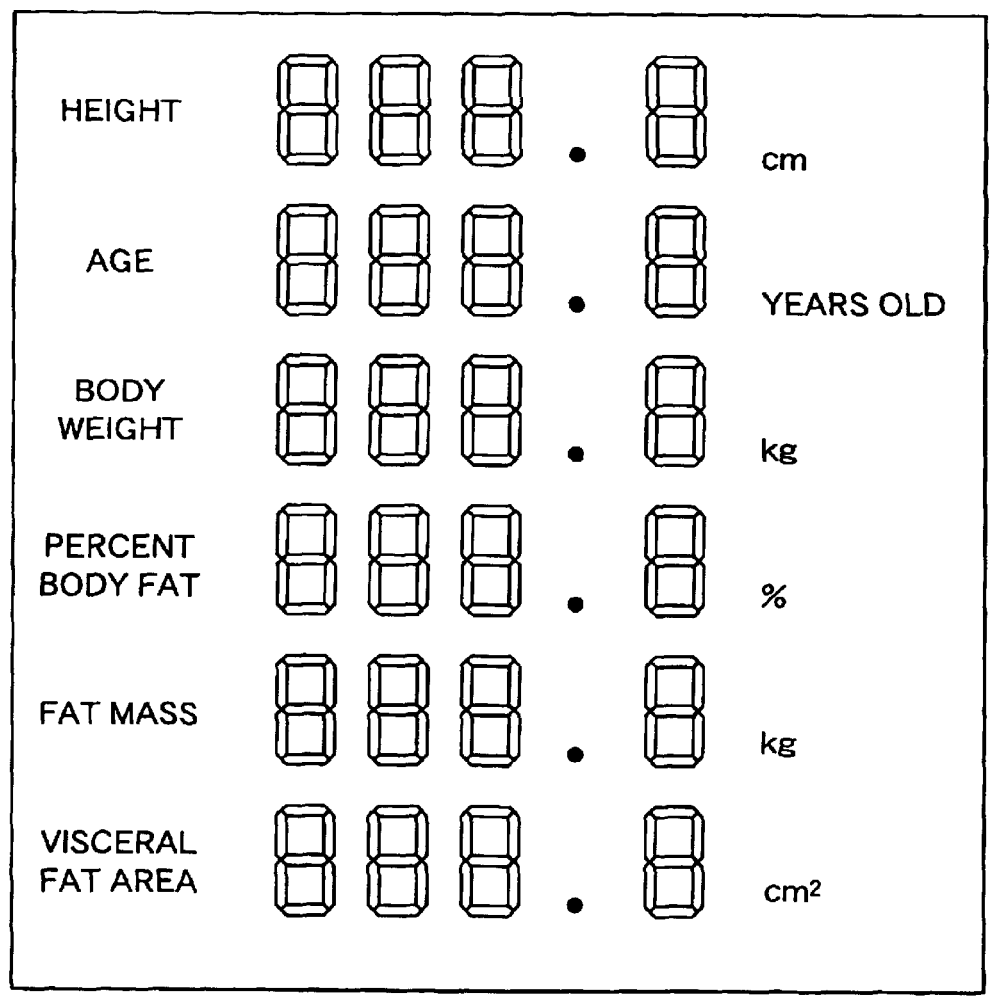
FIG. 4 is a diagram showing an example of measurement values and values calculated from the measurement values displayed on the visceral fat area estimating system of FIG. 1.

In STEP S17, as shown in FIG. 4, the measurement values and the values calculated from the measurement values are displayed on the display unit 9.

In the above embodiment, a scale and an body fat meter are provided. However, in the case of an body fat meter such as a card-type body fat meter which is equipped with no scale, a body weight value can be entered manually by use of the UP key 5a, the DOWN key 5b and the setting key 6. In this case, average body weight values of a male and a female are stored in the memory in advance, and the numeric value is incremented or decremented by means of the UP key 5a and the DOWN key 5b and confirmed as a body weight of an subject by means of the setting key 6. Further, in the case of an ordinary calculator which is not equipped with a percent body fat meter, a percent body fat can be entered manually as in the case of the body weight value. As for a height value, although it is entered manually by means of the keys in the above embodiment, a height measuring device may be used to obtain the value.

According to definition of a percent body fat, a fat mass can be determined once a body weight and the percent body fat are determined. Therefore, if a conventional scale equipped with an body fat meter is available, all input variables of the equation (1) for estimating a visceral fat area can be determined, and a visceral fat area can be estimated by the estimation method of the present invention.

In the estimating system 1 of the above embodiment, a bioelectrical impedance between feet has been measured. However, the present invention is not limited to this, and a bioelectrical impedance between hands or between a hand and a foot may be measured instead.

Figure 12A:
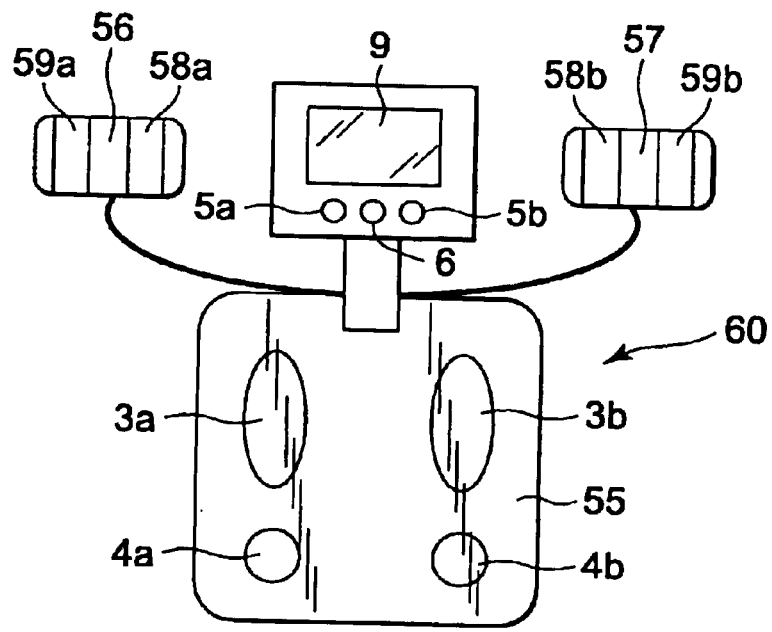
FIGS. 12 A and B are diagrams showing an external configuration of a second embodiment of the system according to the present invention.
Figure 12B:
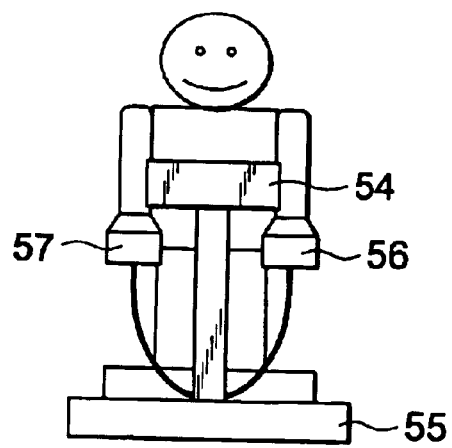

Next, another embodiment of the present invention will be described. FIGS. 12A and B are diagrams showing an external configuration of a second embodiment of the visceral fat estimating system according to the present invention. An estimating system 60 of the present embodiment is different from the first embodiment shown in FIG. 1 in that electrodes 56 and 57 for hands are additionally provided. The same constituents as those in the first embodiment are given the same reference numerals as those given to the constituents in the first embodiment. The electrode 56 for the left hand comprises a constant current applying electrode 58a and a voltage measuring electrode 59a. Similarly, the electrode 57 for the right hand comprises a constant current applying electrode 58b and a voltage measuring electrode 59b.

Figure 13:
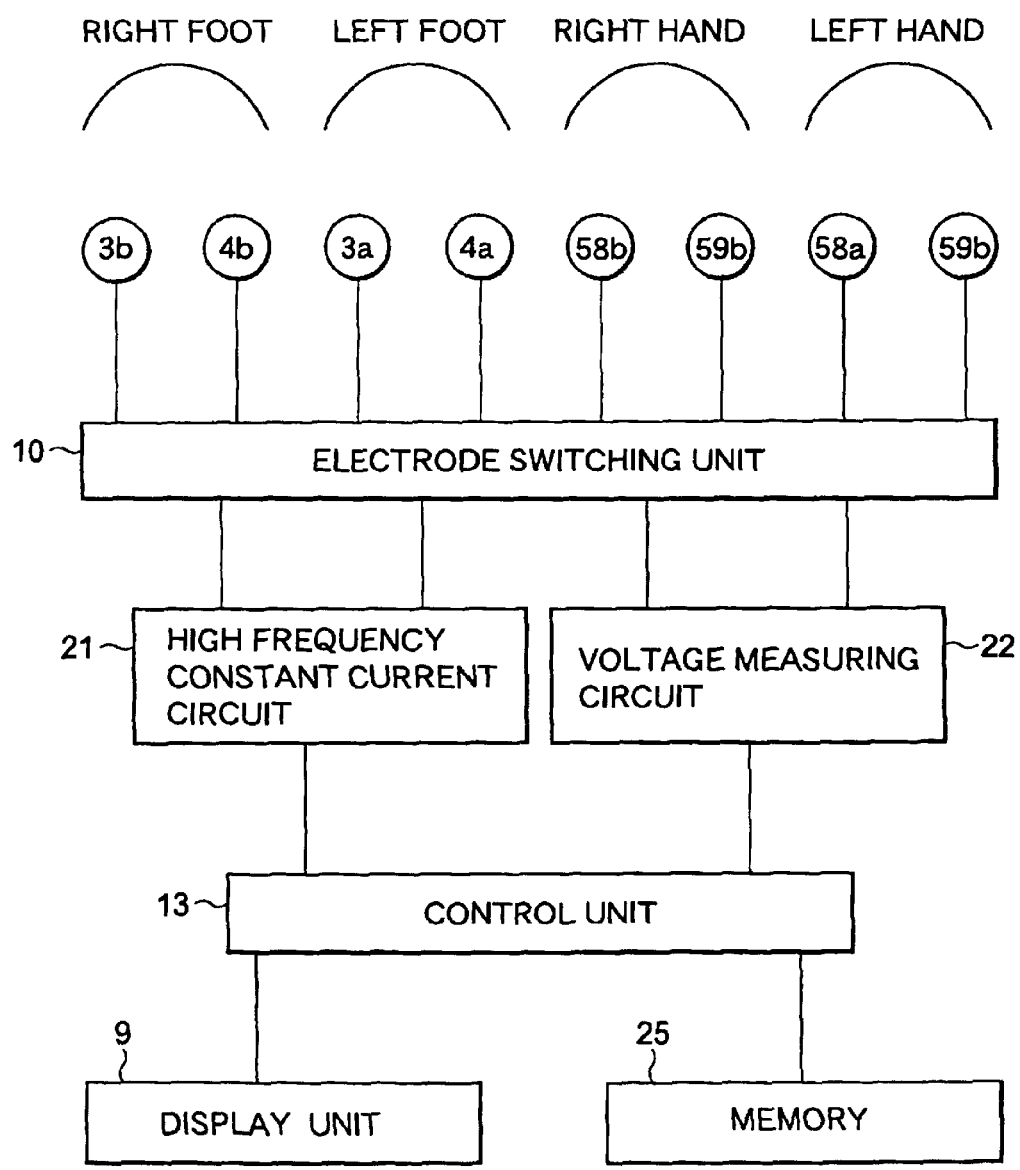
FIG. 13 is a block diagram showing an electric circuit arrangement of the system of FIGS. 12 A and B.

FIG. 13 is an electric block diagram of the estimating system 60 of the present embodiment. Eight electrodes which contact both hands and feet, i.e., electrodes 3a, 3b, 4a, 4b, 58a, 58b, 59a and 59b, are connected to an electrode switching unit 10. The electrode switching unit 10 is connected to a control unit 13 via the high frequency constant current circuit 21 and the voltage measuring circuit 22. The control unit 13 includes a microcomputer and is connected to a memory 25 for storing a variety of data.

Figure 14:
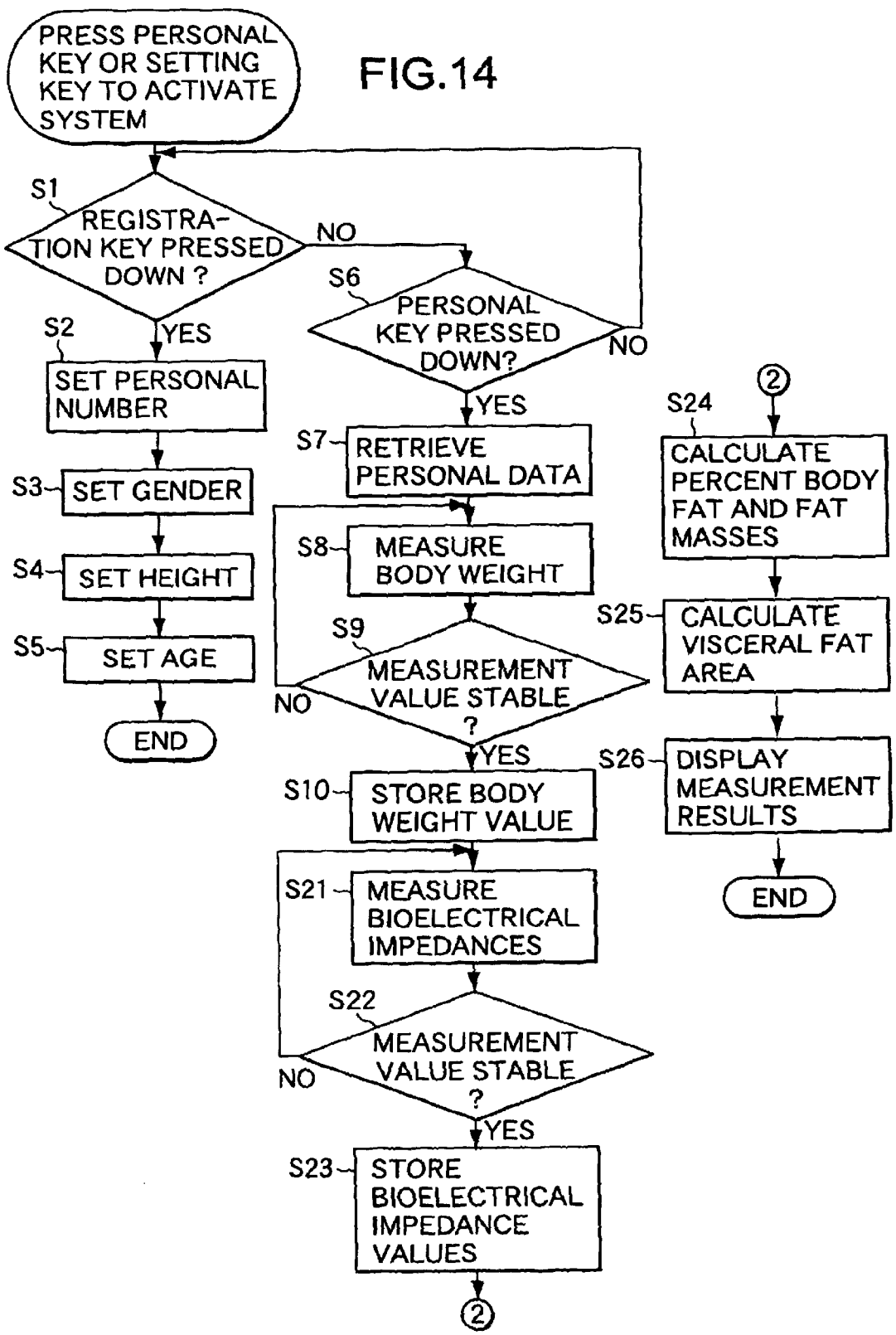
FIG. 14 is a flowchart illustrating steps for making measurements required to estimate a visceral fat area and for estimating the visceral fat area as well as an outline of operations of the system of FIGS. 12 A and B.

Next, operations of the estimating system 60 of the present embodiment will be described with reference to a flowchart in FIG. 14. Steps which perform the same operations as those of steps shown in FIG. 3 are given the same step numbers as those given to the steps of FIG. 3. Descriptions of STEPS S1 to S10 will be omitted since they are the same as STEPS S1 to S10 in FIG. 3.

In STEP S21, the switching unit 10 is switched according to a direction from the control unit 13, whereby an alternating current is supplied from the high frequency constant current circuit 21 to the electrodes 3a and 3b, and voltages are measured at the electrodes 4a and 4b by the voltage measuring circuit 22. Then, the control unit 13 calculates a bioelectrical impedance (BI) from the measured voltages. Thus, BI is measured for a whole body and each of the following body parts, i.e., the right foot, the left foot, the right hand and the left hand. In STEP S22, if a stable measurement value cannot be obtained, the system returns to STEP S21. In STEP S23, the measured BI values are stored in the memory 25.

In STEP S24, percent body fats and fat masses are calculated from the measured BIs. Firstly, a percent body fat and fat mass of the whole body are calculated from the BI of the whole body. Subsequently, a percent body fat, fat free mass and fat mass of each of the right foot, the left foot, the right hand and the left hand are calculated from the BI of each of the right foot, the left foot, the right hand and the left hand, respectively. Then, a total of the fat masses of the body parts is calculated. Thereafter, the total of the fat masses of the body parts is subtracted from the fat mass of the whole body so as to determine a fat mass of a trunk.

In STEP S25, a visceral fat area is estimated by use of the equation (1). As the fat mass FM in the equation, the fat mass of the trunk is used.

In STEP S26, as shown in FIG. 15, the measurement values and the values calculated from the measurement values are displayed on the display unit 9.

The equation (1) for estimating a visceral fat area may take the form of the following equation (2). That is, by use of a visceral fat area VFA as an object variable and a height H, a body weight Wt, a fat mass FM and age AGE as explanatory variables, the following regression equation can be obtained.

$$VFA = C_{21} \times H/Wt + C_{22} \times FM + C_{23} \times Age + C_{24} \qquad (2)$$

wherein $C_{21}$ to $C_{24}$ are constants.

Similarly, the following estimation equations (3) and (4) are also obtained.

$$VFA = C_{31} \times H^3/Wt + C_{32} \times FM + C_{33} \times Age + C_{34} \qquad (3)$$

wherein $C_{31}$ to $C_{34}$ are constants.

$$VFA = C_{41} \times H + C_{42} \times Wt + C_{43} \times FM + C_{44} \times Age + C_{45} \qquad (4)$$

wherein $C_{41}$ to $C_{45}$ are constants.

It is known that as in the case of the equation (1), the constants $C_{21}$ to $C_{24}$, $C_{31}$ to $C_{34}$ and $C_{41}$ to $C_{45}$ vary according to personal parameters including intensity of daily activity, presence or absence of menstruation, age at the onset of menopause and the number of years elapsed after the onset of menopause. Therefore, when a correction is made based on such personal parameters, a visceral fat area can be estimated more accurately.

The present invention estimates a visceral fat area of an subject based on an equation which takes a height, body weight, age and gender of the subject and a fat mass measured by a bioelectrical impedance method of the subject as parameters. Hence, the visceral fat area of the subject can be estimated without concern for exposure of the subject to X-rays.

Further, the above equation of the present invention is expressed as $$VFA = C_1 \times H^2/Wt + C_2 \times FM + C_3 \times Age + C_4$$

when the height is expressed as H, the body weight as Wt, the fat mass as FM, the age as Age, the visceral fat area as VFA and constants as $C_1$, $C_2$, $C_3$ and $C_4$. Therefore, the visceral fat area can be estimated with good accuracy.

Still further, in the above equation of the present invention, a correction is made based on personal parameters of the subject, i.e., intensity of daily activity, presence or absence of menstruation, age at the onset of menopause and the number of years elapsed after the onset of menopause. Thereby, accuracy of estimation of the visceral fat area can be further improved.

In addition, the present invention comprises first input unit for inputting a height of an subject, second input unit for inputting a body weight of the subject, third input unit for inputting a fat mass of the subject, fourth input unit for inputting age of the subject, computation unit for computing a visceral fat area based on data from the first, second, third and fourth input unit, and display unit for displaying the visceral fat area computed by the computation unit. Thereby, accuracy of estimation of the visceral fat area can be improved.

Further, the second and third input unit of the present invention are a scale equipped with an body fat meter. Therefore, the prior art can be used effectively.

Still further, the computation unit of the present invention performs the computation based on an equation expressed as $$VFA = C_1 \times H^2/Wt + C_2 \times FM + C_3 \times Age + C_4$$

when the height of the subject is expressed as H, the body weight as Wt, the fat mass as FM, the age as Age, the visceral fat area as VFA and constants as $C_1$, $C_2$, $C_3$ and $C_4$. Thereby, accuracy of estimation of the visceral fat area can be improved.

Still further, the computation unit of the present invention makes, in the computation of the visceral fat area, a correction based on personal parameters which are intensity of daily activity, presence or absence of menstruation, age at the onset of menopause and the number of years elapsed after the onset of menopause. Thereby, accuracy of estimation of the visceral fat area can be further improved.

As described above, according to the present invention, it is free from a problem of exposure to X-rays and safe since it uses no X-rays. This means that the present invention requires no radiological technician, and therefore it can be practiced easily. As a result, prevention of obesity or a lifestyle-related disease at home and monitoring of progress by an individual becomes possible. Further, since measurement of a circumference right on a navel of an abdominal part is not needed, less errors occur at the time of measurement, the measurement can be carried out more easily, and an subject undergoes less mental stress and can make more accurate measurement by himself/herself. In addition, man-made errors caused by an examiner are decreased, and a visceral fat are can be estimated with proper accuracy.

What is claimed is:

1. A system for estimating a visceral fat area, the system comprising a first input unit, a second input unit, a third input unit, a fourth input, a computation unit and a display unit, wherein said first input unit inputs a height of an subject, said second input unit inputs a body weight of the subject, said third input unit inputs a fat mass of the subject, said fourth input unit inputs age of the subject, said computation unit computes a visceral fat area based on a regression equation which takes the height, body weight, fat mass and age of the subject as parameters inputted from said first, second, third and fourth input unit, and said display unit displays the visceral fat area computed by said computation unit.

2. The system of claim 1, wherein the computation unit performs the computation based on an equation expressed as $$VFA = C_1 \times H^2/Wt + C_2 \times FM + C_3 \times Age + C_4$$

when the height of the subject is expressed as H, the body weight as Wt, the fat mass as FM, the age as Age, the visceral fat area as VFA and constants as $C_1$, $C_2$, $C_3$ and $C_4$.

3. The system of claim 1, wherein the computation unit performs the computation based on an equation expressed as $$VFA = C_{21} \times H/Wt + C_{22} \times FM + C_{23} \times Age + C_{24}$$

when the height of the subject is expressed as H, the body weight as Wt, the fat mass as FM, the age as Age, the visceral fat area as VFA and constants as $C_{21}$, $C_{22}$, $C_{23}$ and $C_{24}$.

4. The system of claim 1, wherein the computation unit performs the computation based on an equation expressed as $$VFA = C_{31} \times H^3/Wt + C_{32} \times FM + C_{33} \times Age + C_{34}$$

when the height of the subject is expressed as H, the body weight as Wt, the fat mass as FM, the age as Age, the visceral fat area as VFA and constants as $C_{31}$, $C_{32}$, $C_{33}$ and $C_{34}$.

5. The system of claim 1, wherein the computation unit performs the computation based on an equation expressed as $$VFA = C_{41} \times H + C_{42} \times Wt + C_{43} \times FM + C_{44} \times Age + C_{45}$$

when the height of the subject is expressed as H, the body weight as Wt, the fat mass as FM, the age as Age, the visceral fat area as VFA and constants as $C_{41}$, $C_{42}$, $C_{43}$, $C_{44}$ and $C_{45}$.

6. The system of any one of claims 1 and 21–24, wherein said third input unit measures a bioelectrical impedance between two body parts of the subject and calculates the fat mass based on the height, body weight and bioelectric impedance of the subject.

7. The system of claim 6, wherein the two body parts are both feet.

8. The system of claim 6, wherein the two body parts are both hands.

9. The system of claim 6, wherein the two body parts are a hand and a foot.

10. The system of any one of claims 1 and 2–5, wherein the fat mass is a fat mass of a trunk.

11. The system of any one of claims 1 and 2–5, wherein in the computation of the visceral fat area, the computation unit makes a correction based on at least one of personal parameters which are intensity of daily activity, presence or absence of menstruation, age at the onset of menopause and the number of years elapsed after the onset of menopause.

12. The system of claim 10, wherein said third input unit measures bioelectric impedances for a whole body and each of body parts of a right foot, a left foot, a right hand and a left hand of the subject, calculates a fat mass of the whole body from the measured bioelectrical impedance of the whole body, calculates fat mass of each of the body parts from the measured bioelectrical impedance of each of the body parts, calculates a total of fat masses of the body parts, and subtracts the total of the fat masses of the body parts from the fat mass of the whole body so at to determine the fat mass of the trunk.

13. The system of claim 6, wherein in the computation of the visceral fat area, the computation unit makes a correction based on at least one of personal parameters which are intensity of daily activity, presence or absence of menstruation, age at the onset of menopause and the number of years elapsed after the onset of menopause.

14. The system of claim 10, wherein in the computation of the visceral fat area, the computation unit makes a correction based on at least one of personal parameters which are intensity of daily activity, presence or absence of menstruation, age at the onset of menopause and the number of years elapsed after the onset of menopause.

* * * * *